United States Patent
Fine et al.

(10) Patent No.: US 8,371,296 B2
(45) Date of Patent: *Feb. 12, 2013

(54) METHOD AND APPARATUS FOR NITRIC OXIDE GENERATION

(75) Inventors: David H. Fine, Cocoa Beach, FL (US); Stephen J. MacDonald, Salem, NH (US); David Rounbehler, Las Cruces, NM (US); David Wheeler, Lunenburg, MA (US); Jonathan L. Rolfe, North Easton, MA (US); George Jarvis, Arlington, MA (US)

(73) Assignee: Geno, LLC, Cocoa, FL (US)

( * ) Notice: Subject to any disclaimer, the term of this patent is extended or adjusted under 35 U.S.C. 154(b) by 1429 days.

This patent is subject to a terminal disclaimer.

(21) Appl. No.: 11/382,116

(22) Filed: May 8, 2006

(65) Prior Publication Data

US 2007/0089739 A1    Apr. 26, 2007

Related U.S. Application Data

(63) Continuation of application No. 10/228,958, filed on Aug. 28, 2002, now Pat. No. 7,040,313.

(60) Provisional application No. 60/316,964, filed on Sep. 5, 2001.

(51) Int. Cl.
*A61M 16/00* (2006.01)
(52) U.S. Cl. ............... 128/203.12; 128/202.26; 204/179
(58) Field of Classification Search .................. 423/405
See application file for complete search history.

(56) References Cited

U.S. PATENT DOCUMENTS

| | | | |
|---|---|---|---|
| 1,021,234 A | 3/1912 | Muller von Berneck et al. | |
| 2,272,810 A | 2/1942 | Denys | |
| 4,007,057 A | 2/1977 | Littauer et al. | |
| 4,010,897 A | 3/1977 | Treharne et al. | |
| 4,287,040 A | 9/1981 | Alamaro | |
| 4,774,069 A | 9/1988 | Handley | |
| 4,778,450 A | 10/1988 | Kamen | |
| 5,228,434 A * | 7/1993 | Fishman | 128/203.12 |
| 5,396,882 A | 3/1995 | Zapol | |
| 5,485,827 A | 1/1996 | Zapol et al. | |
| 5,525,357 A | 6/1996 | Keefer et al. | |
| 5,545,614 A | 8/1996 | Stamler et al. | |
| 5,558,083 A | 9/1996 | Bathe et al. | |
| 5,570,683 A * | 11/1996 | Zapol | 128/200.14 |
| 5,615,669 A * | 4/1997 | Olsson et al. | 128/203.12 |

(Continued)

FOREIGN PATENT DOCUMENTS

| WO | 92/10228 | 6/1992 |
|---|---|---|
| WO | WO 94/16740 | 8/1994 |

(Continued)

OTHER PUBLICATIONS

Mascarenhas, Oscar Carlton, "Epoxy-Based Medical Grade Adhesive Hydrogels and Nitric Oxide Releasing Polymers", *Dissertation Abstracts International*, vol. 55/02-B, pp. 445 (1993).

(Continued)

*Primary Examiner* — Melvin C Mayes
*Assistant Examiner* — Kenneth Vaden
(74) *Attorney, Agent, or Firm* — Steptoe & Johnson LLP

(57) ABSTRACT

Inhalation of low levels of nitric oxide can rapidly and safely decrease pulmonary hypertension in mammals. Precise delivery of nitric oxide at therapeutic levels of 20 to 100 ppm and inhibition of reaction of nitric oxide with oxygen to form toxic impurities such as nitrogen dioxide can provide effective inhalation therapy for pulmonary hypertension.

8 Claims, 1 Drawing Sheet

U.S. PATENT DOCUMENTS

| | | | |
|---|---|---|---|
| 5,651,358 A * | 7/1997 | Briend et al. | 128/203.12 |
| 5,676,963 A | 10/1997 | Keefer et al. | |
| 5,683,668 A * | 11/1997 | Hrabie et al. | 423/405 |
| 5,692,495 A * | 12/1997 | Sheu | 128/203.12 |
| 5,823,180 A * | 10/1998 | Zapol | 128/200.24 |
| 5,827,420 A * | 10/1998 | Shirazi et al. | 205/220 |
| 5,839,433 A * | 11/1998 | Higenbottam | 128/204.21 |
| 5,871,009 A * | 2/1999 | Rydgren et al. | 128/203.12 |
| 5,873,359 A * | 2/1999 | Zapol et al. | 128/203.12 |
| 5,994,444 A * | 11/1999 | Trescony et al. | 524/429 |
| 6,046,383 A | 4/2000 | Elsenga-Boersma et al. | |
| 6,103,275 A | 8/2000 | Seitz et al. | |
| 6,109,260 A | 8/2000 | Bathe | |
| 6,158,434 A | 12/2000 | Lugtigheid et al. | |
| 6,190,704 B1 | 2/2001 | Murrell | |
| 6,261,594 B1 | 7/2001 | Smith et al. | |
| 6,270,779 B1 | 8/2001 | Fitzhugh et al. | |
| 6,758,214 B2 | 7/2004 | Fine et al. | |
| 7,025,869 B2 | 4/2006 | Fine et al. | |
| 7,040,313 B2 * | 5/2006 | Fine et al. | 128/203.12 |
| 2001/0012851 A1 | 8/2001 | Lundy et al. | |
| 2002/0090401 A1 | 7/2002 | Tucker et al. | |
| 2005/0142218 A1 | 6/2005 | Tucker et al. | |

FOREIGN PATENT DOCUMENTS

| | | |
|---|---|---|
| WO | WO 01/15738 A2 | 3/2001 |

OTHER PUBLICATIONS

Pulfer, Sharon Kay, "Nitric Oxide Releasing Polymers and Their Application to Vascular Devices (Polyethyleneimine, Polytetrafluoroethylene)", *Dissertation Abstracts International*, vol. 56/12-B, pp. 6727 (1995).

Roselle, Dominick C., et al., "Characterization and Nitric Oxide Release Studies of Lipophilic 1-Substituted Diazen-1-ium-1,2-Diolates", *Journal of Controlled Release*, vol. 51, pp. 131-142 (1998).

Smith, Daniel J., et al., "Nitric Oxide-Releasing Polymers Containing the [N(O)NO] Group", *Journal of Medicinal Chemistry*, vol. 39, No. 5, pp. 1148-1156 (1996).

Taira, Masafumi, et al. "Continuous Generation System for Low-Concentration Gaseous Nitrous Acid", *Analytical Chemistry*, vol. 62, No. 6, pp. 630-633, (1990).

International Search Report for International Application No. PCT/US02/27278 filed Aug. 28, 2002, 8 pages, Mar. 10, 2004.

Suzuki, "Nitrogen Oxides Generation Method for Recovered Nitric Acid by Electrolysis. An Action Plan for Reduction of Low-Level-Liquid-Waste in Processing Plant", Kyoto Daigaku Genshiro Jikkensho, (Tech. Rep.) (no month, 1991), KURRI-TR-361, pp. 19-26.

Non-final Office Action dated Apr. 8, 2005 for U.S. Appl. No. 10/229,026, filed Aug. 28, 2002; 17 pages.

Tannenbaum, S.R. et al., "Inhibition of Nitrosamine Formation by Ascorbic Acid," *The American Journal of Clinical Nutrition*, American Society of Clinical Nutrition, Bethesda, Maryland, Jan. 1991, vol. 53, pp. 247-250.

Licht, W.R. et al., "Use of Ascorbic Acid to Inhibit Nitrosation: Kinetic and Mass Transfer Considerations for an In Vitro System," *Carcinogenesis*, IRL Press At Oxford University Press, Oxford, Mar. 1988, pp. 365-371.

* cited by examiner

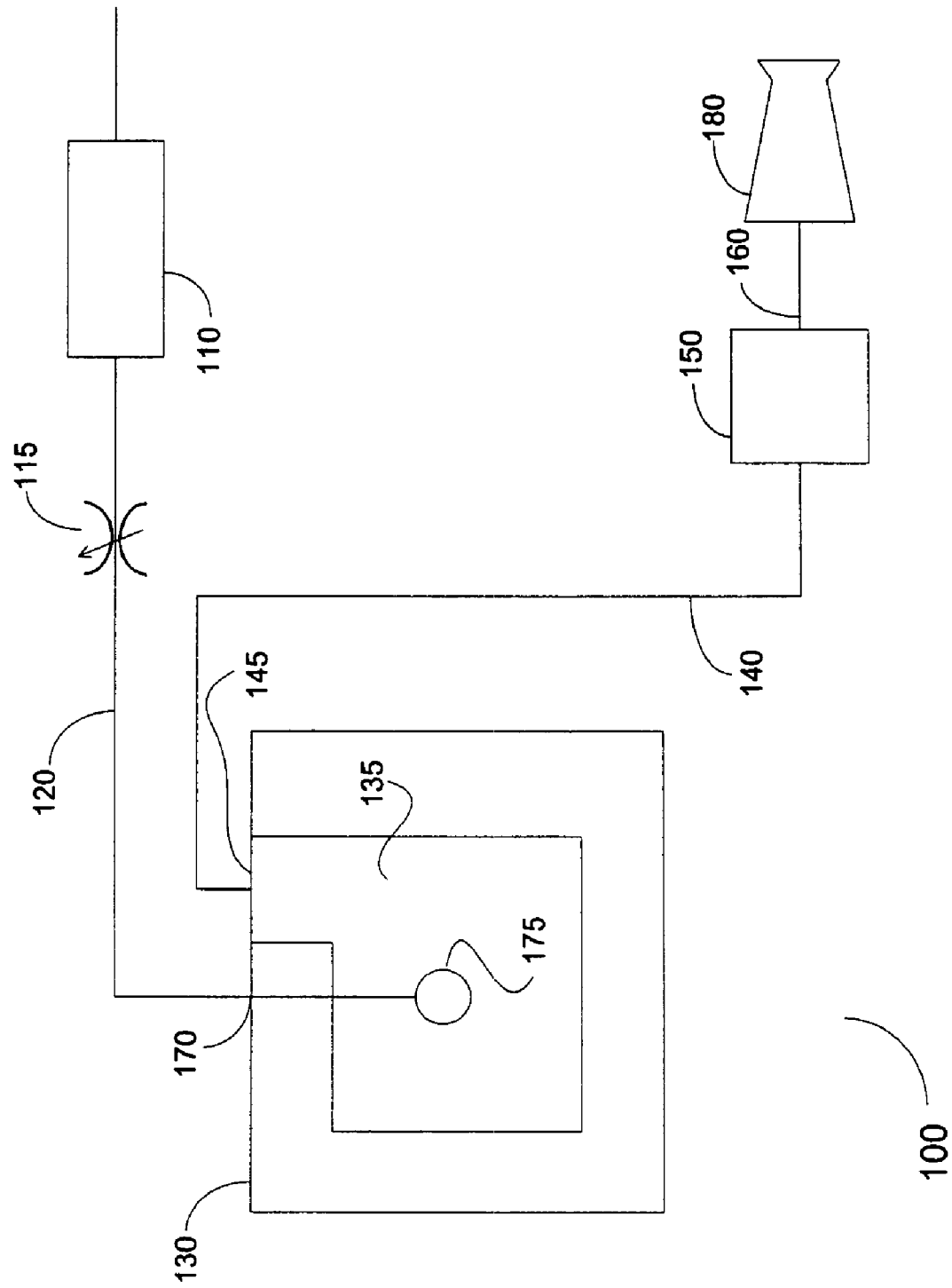

METHOD AND APPARATUS FOR NITRIC OXIDE GENERATION

CLAIM OF PRIORITY

This application is a continuation (and claims the benefit of priority under 35 USC §120) of U.S. application Ser. No. 10/228,958, filed Aug. 28, 2002, now U.S. Pat. No. 7,040,313, which, under 35 USC §119(e)(1), claims the benefit of prior U.S. provisional application no. 60/316,964 filed on Sep. 5, 2001, which is incorporated by reference in its entirety.

CROSS REFERENCE TO RELATED APPLICATIONS

The present application is related to co-pending application Ser. No. 10/228,956 filed Aug. 28, 2002, entitled "Controlled Generation of Nitric Oxide," co-pending application Ser. No. 11/279,029 filed Apr. 7, 2006, entitled "Nitric Oxide Delivery System", and U.S. Pat. No. 7,025,869 issued on Apr. 11, 2006, entitled "Nitric Oxide Delivery System," each of which are incorporated by reference in its entirety.

TECHNICAL FIELD

This document relates to an apparatus and a method for controllably generating nitric oxide.

BACKGROUND

Nitric oxide plays an important role in the regulation of biochemical pathways in living organisms. The inhalation of low levels (20 to 100 ppm) of nitric oxide has been shown to have a major therapeutic value in treatment of a diverse range of disorders ranging from reversible and irreversible pulmonary hypertension to treatment of neonates exhibiting hypoxemic respiratory failure and persistent pulmonary hypertension. Conventional medical uses of nitric oxide gas can involve dilution of a nitric oxide gas stream with gases immediately before administration of the nitric oxide gas to a mammal. Precise delivery of nitric oxide at therapeutic levels of 20 to 100 ppm and inhibition of reaction of nitric oxide with oxygen to form toxic impurities such as nitrogen dioxide gas is needed for effective inhalation therapy.

SUMMARY

Nitric oxide, also known as nitrosyl radical, is a free radical that is an important signaling molecule in pulmonary vessels. Nitric oxide can moderate pulmonary hypertension caused by elevation of the pulmonary arterial pressure. Inhaling low concentrations of nitric oxide, for example, in the range of 20-100 ppm can rapidly and safely decrease pulmonary hypertension in a mammal by vasodilation of pulmonary vessels.

Some disorders or physiological conditions can be mediated by inhalation of nitric oxide. The use of low concentrations of inhaled nitric oxide can prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma and status asthmaticus or hypoxia. Nitric oxide can also be used to treat chronic pulmonary hypertension, bronchopulmonary dysplasia, chronic pulmonary thromboembolism and idiopathic or primary pulmonary hypertension or chronic hypoxia. Advantageously, nitric oxide can be generated and delivered in the absence of harmful side products, such as nitrogen dioxide. The nitric oxide can be generated at a concentration suitable for delivery to a mammal in need of treatment.

In one aspect, an apparatus for delivering a therapeutic gas including nitric oxide includes a receptacle including a therapeutic gas outlet and a non-electrolytic nitric oxide precursor receiver and a transport gas inlet fluidly communicating from a source of a transport gas to the therapeutic gas outlet through the non-electrolytic nitric oxide precursor receiver. The therapeutic gas delivery system can be fluidly connectable to the therapeutic gas outlet. The therapeutic gas delivery system can include a gas purifier which can be, for example, a filter. The therapeutic gas delivery system can include a mask fluidly connectable to the therapeutic gas outlet that can be connectable to a mammal.

In another aspect, a method of delivering nitric oxide to a mammal includes non-electrolytically generating a therapeutic gas from a nitric oxide precursor, wherein the therapeutic gas includes nitric oxide and is substantially devoid of nitrogen dioxide and transporting the therapeutic gas to a mammal. Non-electrolytically generating the therapeutic gas can include contacting the nitric oxide precursor with a buffer solution to form a mixture. The buffer solution can be a pH buffer combination. The pH buffer combination can include acetic acid/acetate, hydrochloric acid/chloride, hydrochloric acid/citrate, citric acid-phosphate, phosphoric acid/phosphate or citric acid/citrate. The pH of the mixture can be in the range of 4 to 7 or 6.5 to 6.9. The nitric oxide precursor can be a nitrite salt. The nitrite salt can be, for example, sodium nitrite. The transport gas can be, for example, swept over the mixture. The therapeutic gas can deliver, for example, 20 to 60 ppm nitric oxide to the mammal. The transport gas can be oxygen, ambient air or a mixture of air and oxygen. The nitric oxide can be released from the precursor for over at least an hour. The therapeutic gas can be substantially devoid of nitrogen dioxide.

In another aspect, a kit includes a nitric oxide precursor and instructional material describing a method of generating a therapeutic gas and transporting the therapeutic gas, the therapeutic gas comprising nitric oxide and being substantially devoid of nitrogen dioxide. The nitric oxide precursor can be a nitrite salt. The nitrite salt can be, for example, sodium nitrite. The nitric oxide can be released from the precursor for over at least an hour. Other features or advantages will be apparent from the following detailed description of several embodiments, and also from the appended claims.

DESCRIPTION OF DRAWING

FIG. 1 is a drawing depicting a schematic view of a nitric oxide generation and delivery system.

DETAILED DESCRIPTION

Various nitric oxide precursors can be used in a nitric oxide delivery system. Nitric oxide precursors can include a nitrogen-containing compound with a structure X-nitric oxide, when X is an organic residue or a precursor salt. For example, the nitric oxide precursor can include an alkali metal nitrite, an alkaline earth metal nitrite, a transition metal nitrite or an ammonium nitrite, for example, potassium nitrite, sodium nitrite, rubidium nitrite, strontium nitrite, barium nitrite, calcium nitrite, copper nitrite, zinc nitrite, or mixtures thereof. The nitric oxide precursor can include nitrogen-containing acids, such as nitric acid. Physical characteristics of the nitric oxide precursor, such as the dissolution rate, can be used to control delivery of nitric oxide.

The nitric oxide precursor can be dissolved in a solution in which the precursor can dissociate to form anions, including nitrite anions, and cations. The solution can include a buffer solution. A buffer solution can include a pH buffer combination which is a solution containing either a weak acid or a weak base at a concentration that renders the solution resistant to change in pH. The buffer solution provides a source of hydrogen cations, which can combine with the nitrite anions to form nitrous acid ($HNO_2$). Nitrous acid can decompose into several products in water. One of these products is nitric oxide. The reactions are summarized below in equations (I), (II) and (III):

$$NaNO_2 \leftrightarrows Na^+ + NO_2^- \quad \text{(I)}$$

$$NO_2^- + H^+ \leftrightarrows HNO_2 \quad \text{(II)}$$

$$3HNO_2 \leftrightarrows H_2O + H^+ + NO_3^- + 2NO \quad \text{(III)}$$

The nitric oxide precursor can include sodium nitrite, which dissociates into sodium cations and nitrite anions, as shown in equation (I). The nitrite anions in the buffer solution can form nitrous acid as shown in equation (II), which can decompose into water, nitrate and hydrogen ions and two molecules of gaseous nitric oxide, as shown in equation (III).

The generated nitric oxide gas formed by the above reactions has a low solubility in the pH buffer combination (e.g., 0.00983 g nitric oxide per liter at 0° C.; 4.6 mL/100 mL at 20° C. in water (Merck Index, 10th Edition, 1983)). The relatively insoluble nitric oxide can be removed from the solution by a transport gas stream to form a therapeutic gas. The transport gas can be 100% oxygen, a mixture of air and oxygen or ambient air. The transport gas stream can be bubbled, otherwise distributed through the solution or swept over the headspace of the solution. Other byproducts such as, for example, nitrous acid and nitrogen dioxide, can be volatile and can be carried with the transport gas stream along with nitric oxide formed in the reaction.

When delivering nitric oxide for therapeutic use to a mammal, it can be important to avoid delivery of nitrogen dioxide to the mammal. Nitrogen dioxide can be formed by the oxidation of nitric oxide with oxygen. The rate of formation of nitrogen dioxide is proportional to the square power of the nitric oxide concentration and the first power of the oxygen concentration. Reducing the nitric oxide concentration by a factor of ten reduces the nitrogen dioxide concentration by a factor of one hundred. Thus, by limiting the nitric oxide concentration in a therapeutic gas, the therapeutic gas can be substantially devoid of nitrogen dioxide. For example, when nitric oxide concentration in the transport gas is below 100 ppm, the resulting therapeutic gas generated from the nitric oxide precursor in a solution is substantially devoid of nitrogen dioxide.

In certain circumstances, the concentration of nitric oxide generated in the therapeutic gas is controlled, for example, by the concentration of nitric oxide precursor provided to the solution, the concentration of hydrogen cations in the solution, and the characteristics of the pH buffer combination. Other factors that can affect the nitric oxide concentration in the therapeutic gas can include, for example, physical form of the nitric oxide precursor, presence of a reduction-oxidation reaction in an optional gas purifier, and rate of flow of the transport gas through the solution.

The concentrations of hydrogen cations and the nitric oxide precursor can control the rate of generation of nitric oxide. Since the concentration of nitric oxide is low, about 20 to 100 ppm, reaction conditions, that increase the concentration of nitric oxide precursor and decrease the concentration of hydrogen ions lead to a stoichiometrically inefficient reaction. Decreasing the concentration of hydrogen ions, for example, by using a weak acid, shifts the equilibrium in equation (II) toward the nitrite anions. A reservoir of nitrite ions can be created such that the nitrous acid concentration is maintained at a relatively constant level.

Referring to FIG. 1, a nitric oxide delivery system 100 for producing a therapeutic gas including nitric oxide includes a transport gas pump 110, a restrictor valve 115, a tube 120, and a receptacle 130. The pump can be a diaphragm pump. The receptacle 130 includes a non-electrolytic nitric oxide precursor receiver 135. The non-electrolytic nitric oxide precursor receiver is a receiver that does not require application of voltage for the nitric-oxide generating reaction to proceed. The non-electrolytic nitric oxide precursor receiver includes a transport gas inlet 170 and a therapeutic gas outlet 145. The therapeutic gas outlet 145 is connectable to a gas delivery system, which includes a tube 140, an optional gas purifier 150, a tube 160, and a mask 180. The mask 180 is connectable to a mammal. The transport gas inlet 170 includes a gas distributor 175. The gas distributor 175 distributes the transport gas in the receiver 135. The gas distributor 175 can be a mechanical agitator, which can include, for example, a stirrer, a vibrator, a sparger and a bubbler to prevent supersaturation of nitric oxide in the receiver 135. The a transport gas pump 110 controls flow rate of a transport gas through the receiver. For example, the flow rate can be from 1 to 10 liters per minute, 2-8 liters per minute or 2 to 5 liters per minute. The flow rate of the transport gas can be in the range of 1 to 20 liters per minute. The transport gas can be 100% oxygen, a mixture of air and oxygen, or ambient air. The rate of flow of transport gas in the reaction vessel can affect the generation of nitric oxide. Mechanical agitation using, for example, stirring, vibration, or bubbling the transport gas through the solution, sweeping the transport gas over the solution or other methods of agitation enhances the transport of nitric oxide in the therapeutic gas.

In a general process for delivering nitric oxide, the a transport gas pump 110 conveys a stream of transport gas at a specific flow rate, into and through the tube 120 and into and through the non-electrolytic nitric oxide precursor receiver 135, which contains the nitric oxide precursor and buffer solution. The non-electrolytic nitric oxide precursor receiver 135 can be, for example, filled to half the capacity with the nitric oxide precursor and the buffer solution, for example, a pH buffer combination. The pH buffer combination can be used to control the pH of the solution to very close to pH 7 to maintain a concentration of hydrogen ions suitable to control nitric oxide production from the solution. Suitable pH buffers include, for example, combinations of acetic acid and acetate salt (acetic acid/acetate), combinations of hydrochloric acid and chloride salt, combinations of hydrochloric acid and citrate salt (hydrochloric acid/citrate), combinations of citric acid and phosphate salt (citric acid-phosphate), combinations of phosphoric acid and phosphate salt (phosphoric acid/phosphate) and combinations of citric acid and citrate salt (citric acid/citrate). A pH within the range of 4.5-7.0, or the range of 6.5-6.9, can be maintained in the solution using the pH buffer combination.

Nitric oxide is generated in the nitric oxide precursor receiver 135. The stream of transport gas carries the generated nitric oxide as the therapeutic gas into and through tube 140 into (optionally) a gas purifier 150. If necessary, the therapeutic gas can pass into and through the optional gas purifier 150 which can remove any residual impurities such as nitrogen dioxide and nitrous acid, if present. The therapeutic gas including the nitric oxide is transported in the transport gas into and through tube 160 to mask 180 to the mammal. The mask 180 can include any device or implement that is used to provide the nitric oxide stream to the mammal and is typically selected by the physician based on the mammal need and condition. For example, the mask 180 can be in the form of a tight-fitting or a loose fitting mask, an intubation tube, a nasal delivery tube, or a tube that generally directs the nitric oxide gas in the region around the mammal's mouth and/or nose.

In certain circumstances, the therapeutic gas can be passed through a nitric oxide releasing solution. A nitrite releasing salt assists in the generation of nitric oxide from the nitric oxide precursor. For example, a second salt, such as a nitric oxide-releasing reactant, can be added to the solution. A nitric oxide-releasing reactant, for example, an iodide salt or ferrous salt, assists the production of nitric oxide as shown below:

$$2NO_2^- + 2I^- + 4H^+ \rightarrow I_2 + 2H_2O + 2NO$$

or $$2NO_2^- + 2Fe^{+2} + 6e^- \rightarrow 2Fe^{+3} + 2H_2O + 2NO$$

For example, the nitric oxide-releasing reactant can be 1 molar ferrous sulfate solution or 10% wt/wt aqueous solution of sodium iodide. The nitrite releasing salt can include salts of Groups I, II, III, IV, V, VI and VII of the periodic table. For example, the nitrite releasing salt can include a ferrous salt.

In certain circumstances, the therapeutic gas can be passed through an optional therapeutic gas purifier 150. When the therapeutic gas stream contacts the optional therapeutic gas purifier, residual impurities, such as nitrous acid and nitrogen dioxide, are removed from the therapeutic gas stream. The optional gas purifier can include a filter, which can be, for example, a semi-permeable membrane or barrier, a scrubbing solution, a reduction-oxidation solution, or a pyrolizer. The semi-permeable membrane is a barrier which allows the nitric oxide to pass and retains the impurities. The scrubbing solution is a solution that removes impurities by neutralizing them, for example, a solution of 10% sodium bicarbonate, a 1M ferrous salt solution or an acidified 1M ferrous sulfate solution. A series of aqueous reservoirs can be used to completely decompose the nitrous acid and dissolve any nitric acid or nitrogen dioxide impurities. The reduction-oxidation solution contains a reduction-oxidation agent, which converts impurities completely into nitric oxide. The reduction-oxidation agent can include a ferrous salt. The pyrolizer is a chamber or other component which decomposes the impurities such as nitrous acid and nitrogen dioxide by irradiation or heating. A catalyst, for example, platinum, nickel or silver, can be used to decrease the pyrolysis temperature. For example, the impurities such as nitrous acid and nitrogen dioxide can be passed through a 12 inch long silver tube, 1/8 inch in diameter, heated at 800° C. at a flow rate of 1L/minute. The removal of impurities can be enhanced by using a convoluted or a long path for conducting the therapeutic gas stream through the filter. Additionally, the surface-to-volume ratio of the bubbles can be increased for effective filtration of impurities. For example, a gas sparger can be used to make smaller bubbles.

Alternatively, filter media can also be coated onto a filter or walls of a tube, which can produce a dry therapeutic gas stream upon filtration.

A detector can be included in the therapeutic gas delivery system to detect the concentration of nitric oxide in the therapeutic gas stream. The detector can also detect the concentration of nitrogen dioxide in the therapeutic gas, if necessary, and may provide a warning if the nitric oxide concentration is outside a predetermined range or if the concentration of nitrogen dioxide is above a threshold value. Examples of monitoring techniques include chemiluminescence and electrochemical techniques, and are discussed in, for example, in Francoe et al., "Inhaled nitric oxide: Technical Aspects of Administration and Monitoring," *Critical Care Medicine*, 24(4): 782-796 (1998) which is incorporated by reference in its entirety. The presence of nitric oxide can be detected by for example, a modified version of a Thermo-Electron chemiluminescence (CL) detector.

A kit includes the nitric oxide precursor and instructional material describing a method of generating the therapeutic gas and transporting the therapeutic gas in the transport gas. The therapeutic gas including nitric oxide is substantially devoid of impurities such as nitrogen dioxide.

A therapeutic gas can contain at least 1 ppm of nitric oxide. The therapeutic gas can include less than 100 ppm of nitric oxide. For example, the nitric oxide concentration in the therapeutic gas can be from 20 to 100 ppm. The nitric oxide can be released from the precursor over a period of time ranging from 1 minute to 7 days, 2 days to 3 days, or two hours to twenty four hours.

Oxidation-reduction reactions can assist in the production of nitric oxide. For example, a second salt, such as a nitric oxide-releasing reactant, can be added to the solution. A nitric oxide-releasing reactant, for example, an iodide salt or ferrous salt, assists the production of nitric oxide as shown below:

$$2NO_2^- + 2I^{31} + 4H^+ \rightarrow I_2 + 2H_2O + 2NO$$

or $$2NO_2^- + 2Fe^{+2} + 6e^- \rightarrow 2Fe^{+3} + 2H_2O + 2NO$$

For example, the nitric oxide-releasing reactant can be a 1 molar ferrous sulfate solution or a 10 wt % aqueous solution of sodium iodide. The following examples describe nitric oxide generation.

EXAMPLE 1

Using an apparatus depicted in FIG. 1, a pH buffer combination (100 mL) was prepared which was 1M acetic acid and 1M acetate with a pH of 4.9 and added to a non-electrolytic nitric oxide precursor receiver. Twenty grams of sodium nitrite (approximately 2M) was added to the receiver and the mixture was stirred at room temperature. A transport gas pump equipped with a restrictor valve was used to establish a flow rate of 2 liters per minute of ambient air at 20° C. The transport gas swept the headspace of the nitric oxide receiver to generate the therapeutic gas. The output of nitric oxide generated was 50 ppm in the therapeutic gas, which remained constant at 50 ppm +/−20 ppm for five hours.

EXAMPLE 2

Using an apparatus depicted in FIG. 1, a pH buffer combination (100 mL) was prepared which was 3M acetic acid and 3M acetate with a pH of 4.9 was added to a non-electrolytic nitric oxide receiver. Twenty grams of sodium nitrite (approximately 2M) was added to the receiver and the reaction was stirred at room temperature. A transport gas pump equipped with a restrictor valve was used to establish a flow rate of 2 liters per minute of ambient air at 20° C. The transport gas swept the headspace of the nitric oxide reciever to generate the therapeutic gas. The output of nitric oxide generated was 50 ppm in the therapeutic gas, which remained constant at 50 ppm +/−20 ppm for nine hours.

EXAMPLE 3

Using an apparatus depicted in FIG. 1, a solution was prepared in a non-electrolytic nitric oxide precursor receiver, by dissolving 28 grams of sodium hydrogen phosphate dibasic ($Na_2HPO_4$) in 100 mL of water. Sodium nitrite (15 g) was added to the solution, followed by addition of 40 g of sodium hydrogen phosphate monobasic ($NaH_2PO_4$) until the solution became clear. The total volume of the solution was adjusted to 150 mL. The pH of the solution was approximately 4. In the optional gas purifier, a 0.1 mole of ferrous sulfate ($FeSO_4$) was dissolved in 100 mL of water. A transport gas pump equipped with a restrictor valve was used to establish a flow rate of 2 liters per minute of ambient air at 20° C. The transport gas swept the headspace of the nitric oxide receiver to generate the therapeutic gas. The output of nitric oxide generated in the therapeutic gas was 60 ppm in the therapeutic gas, for a period of seven days.

EXAMPLE 4

Using an apparatus depicted in FIG. 1, a pH buffer combination and nitric oxide precursor mixture was prepared by adding 0.1 mole sodium phosphate monobasic, 0.1 mole sodium phosphate dibasic and 20 g of sodium nitrite to 100 mL of water. The pH of the solution was approximately 5.6. A gas flow controller equipped with a restrictor valve was used to establish a flow rate of 2 liters per minute of ambient air at 20° C. The transport gas was swept over the headspace of the nitric oxide precursor receiver to produce 1% nitric oxide and 99% nitrous acid gas stream. The gas stream was bubbled through an optional gas purifier, which contained a 1M sulfuric acid and 1M ferrous sulfate solution by mixing 0.1 mole of sulfuric acid and 0.1 mole of ferrous sulfate to 100 mL of water. The output of nitric oxide generated was constant in the therapeutic gas, for a period of several days. The therapeutic gas was substantially devoid of nitrogen dioxide.

EXAMPLE 5

Using an apparatus depicted in FIG. 1, a aqueous solution of 2 grams of sodium nitrite, and pH buffer combination of 0.1 mole acetic acid and 0.1 mole sodium acetate was preprared in 100 mL of water. The solution was added to a non-electrolytic nitric oxide precursor receiver and the mixture was stirred. A diaphragm pump equipped with a restrictor valve established a flow rate of 2 liters per minute of ambient air at 20° C. The transport gas swept the headspace of the nitric oxide receiver to generate the therapeutic gas. The output of nitric oxide generated was 50 ppm in the therapeutic gas, which remained constant at 50 ppm +/−20 for five hours.

EXAMPLE 6

Using the apparatus depicted in FIG. 1, a pump equipped with a restrictor valve was used to supply 20° C. ambient air at a flow rate of 2 L/min. Sodium nitrite (15 g) was added to the receiver containing 100 mL of an aqueous solution of a buffer including 28 g of sodium hydrogen phosphate and 40 g of sodium phosphate monobasic. The solution was stirred at room temperature (18-22° C.). The transport gas, air, was swept over the headspace of the receiver into a gas purifier containing nitric oxide releasing agent 100 mL of 1molar iron (II) sulfate ($FeSO_4$) and 4 mL of $H_2SO_4$ to remove impurities.

EXAMPLE 7

Using the apparatus depicted in FIG. 1, a pump was equipped with a restrictor valve to supply 20° C. ambient air at a flow rate of 2 L/min. An aqueous solution (100 mL) was prepared of 15 g of the nitric oxide precursor sodium nitrite and a buffer consisting of 28 g of sodium phosphate ($Na_2HPO_4$) and 40 g of sodium phosphate monobasic ($NaH_2PO_4$) was placed in the receiver. The reaction was stirred at room temperature (18-22° C.). The transport gas, air was swept over the headspace of the receiver into a gas purifier containing nitric oxide releasing agent as shown in Table 1.

TABLE 1

| Experiment | Nitric oxide releasing agent |
|---|---|
| Experiment 1 | 100 mL water, 5 g NaI, 2 mL $H_2SO_4$ |
| Experiment 2 | 100 mL water + 5 g NaI + 2 mL $H_2PO_4$ |
| Experiment 3 | 100 mL Potassium Biphthalate/hydrochloric acid pH 3 buffer + 5 g NaI |
| Experiment 4 | 100 mL 1 M $NaH_2PO_4$ + 5 g NaI. |

Other embodiments are within the scope of the following claims.

What is claimed is:

1. An apparatus for delivering a therapeutic gas including nitric oxide comprising:
   a receptacle including a non-electrolytic nitric oxide precursor receiver;
   the non-electrolytic nitric oxide precursor receiver including a transport gas inlet and a therapeutic gas outlet; and
   the transport gas inlet fluidly communicating from a source of a transport gas to the therapeutic gas outlet through the non-electrolytic nitric oxide precursor receiver,
   wherein the transport gas inlet includes a gas distributor in the non-electrolytic nitric oxide precursor receiver.

2. The apparatus of claim 1 wherein the non-electrolytic nitric oxide precursor receiver is configured to receive a non-electrolytic nitric oxide precursor that includes a precursor salt.

3. The apparatus of claim 1 further including a therapeutic gas delivery system fluidly connectable to the therapeutic gas outlet.

4. The apparatus of claim 3 wherein the therapeutic gas delivery system includes a therapeutic gas purifier.

5. The apparatus of claim 4 wherein the therapeutic gas purifier includes a filter.

6. The apparatus of claim 3 wherein the therapeutic gas delivery system includes a mask fluidly connectable to the therapeutic gas outlet.

7. The apparatus of claim 6 wherein the mask is connectable to a mammal.

8. The apparatus of claim 1 wherein the source of the transport gas includes a gas flow controller.

* * * * *